(12) United States Patent
Chen

(10) Patent No.: US 11,872,184 B2
(45) Date of Patent: Jan. 16, 2024

(54) STEAM PHYSIOTHERAPY MECHANISM

(71) Applicant: Wenjun Chen, New Taipei (TW)

(72) Inventor: Wenjun Chen, New Taipei (TW)

(*) Notice: Subject to any disclaimer, the term of this patent is extended or adjusted under 35 U.S.C. 154(b) by 411 days.

(21) Appl. No.: 17/365,632

(22) Filed: Jul. 1, 2021

(65) Prior Publication Data

US 2023/0000720 A1  Jan. 5, 2023

(51) Int. Cl.
*A61H 33/06* (2006.01)
*A61H 33/00* (2006.01)
*A61L 2/00* (2006.01)

(52) U.S. Cl.
CPC .......... *A61H 33/06* (2013.01); *A61H 33/005* (2013.01); *A61L 2/0047* (2013.01); *A61H 2033/0037* (2013.01); *A61H 2033/0041* (2013.01); *A61H 2033/0083* (2013.01); *A61H 2033/068* (2013.01); *A61L 2202/11* (2013.01)

(58) Field of Classification Search
CPC .................. A61H 33/06; A61H 33/005; A61H 2033/0037; A61H 2033/0041; A61H 2033/0083; A61H 2033/068; A61L 2/0047; A61L 2202/11
USPC ........................................................... 4/524
See application file for complete search history.

(56) References Cited

U.S. PATENT DOCUMENTS

| 4,425,672 | A | 1/1984 | Johnson et al. | |
|---|---|---|---|---|
| 6,339,854 | B1 | 1/2002 | Amendt | |
| 6,615,419 | B1 | 9/2003 | Chang | |
| 9,226,873 | B2 | 1/2016 | Chen | |
| 2006/0260037 | A1* | 11/2006 | Chen | A61H 33/06 4/524 |
| 2007/0294819 | A1* | 12/2007 | Levesque | A61H 33/066 392/416 |
| 2013/0042402 | A1* | 2/2013 | Parker | A61H 33/066 4/524 |
| 2014/0157511 | A1* | 6/2014 | Shurtleff | A61H 33/063 4/524 |

* cited by examiner

*Primary Examiner* — Huyen D Le
(74) *Attorney, Agent, or Firm* — Browdy and Neimark, PLLC

(57) ABSTRACT

A steam physiotherapy mechanism includes a receptacle having a chamber formed in a housing, a steam pipe disposed in the housing, a steam generating device connected to the steam pipe for generating and supplying a steam into the chamber of the housing, a number of tiles disposed in the housing, and a number of retainers engaged with the tiles for anchoring the tiles in the housing, the tiles each include a number of casings each having a compartment, and one or more of the compartments of the casings are filled with an ore mud. The tiles each include a number of passages formed in the casings and communicating with the compartments of the casings.

17 Claims, 10 Drawing Sheets

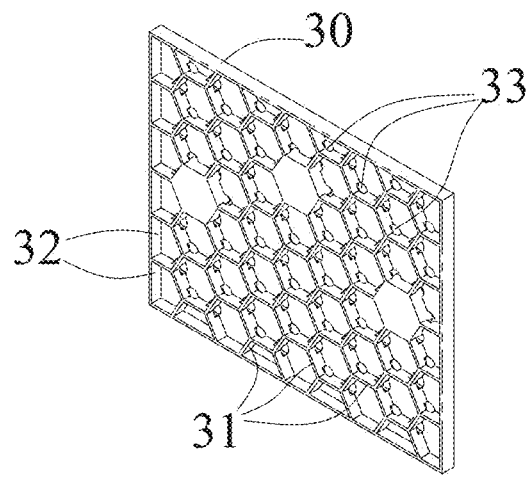
F I G. 9
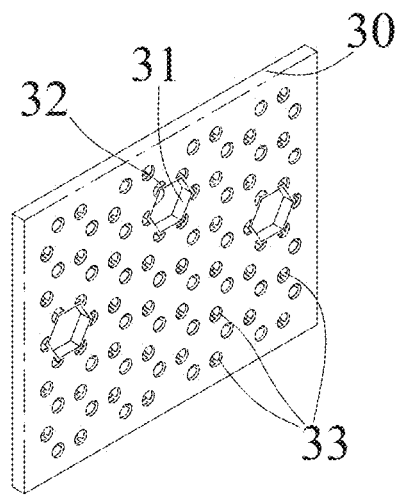
F I G. 10
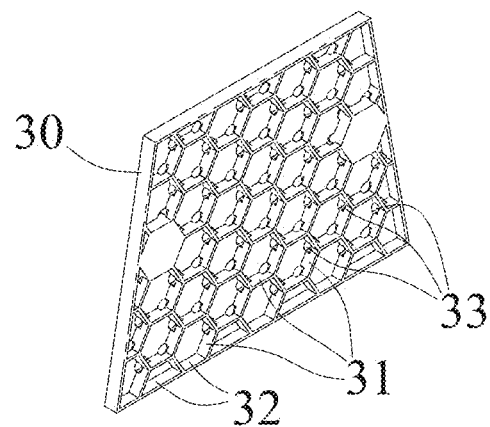
F I G. 11

STEAM PHYSIOTHERAPY MECHANISM

BACKGROUND OF THE INVENTION

1. Field of the Invention

The present invention relates to a steam physiotherapy mechanism, and more particularly to a steam physiotherapy mechanism including a number of tourmaline tiles that may be removed or detached or disengaged from the outer receptacle for allowing the tourmaline tiles to be easily cleaned or replaced or changed with the new ones quickly and readily.

2. Description of the Prior Art

Various kinds of typical steam physiotherapy mechanisms or apparatuses have been developed and provided for steaming bath or the like and for forcefully compressing and permeating a heat energy into the user's skin and for forcing the sweat to flow out of the user's body under the condition that is normally referred to as "surface-layer sweat" or "cold sweat".

For example, U.S. Pat. No. 4,425,672 to Johnson et al., U.S. Pat. No. 6,339,854 B1 to Amendt, U.S. Pat. No. 6,615,419 B1 to Chang, and U.S. Pat. No. 9,226,873 to Chen disclose several of the typical steam physiotherapy apparatuses each comprising an outer housing or outer receptacle for receiving or accommodating the user therein, and some of the typical steam physiotherapy apparatuses may include a number of tourmaline tiles disposed or engaged into the outer housing or outer receptacle for releasing far infrared rays and negative ions into the outer housing or outer receptacle in order to help removal of toxins from the user's body via capillaries and sweat glands.

However, the tourmaline tiles are normally solidly and firmly attached or mounted or secured in the outer receptacle and may not be easily and quickly and readily removed or detached or disengaged from the outer receptacle such that the tourmaline tiles may not be easily and quickly cleaned or replaced or changed with the new ones by the user.

The present invention has arisen to mitigate and/or obviate the afore-described disadvantages of the conventional steam physiotherapy mechanisms.

SUMMARY OF THE INVENTION

The primary objective of the present invention is to provide a steam physiotherapy mechanism including a number of tourmaline tiles that may be removed or detached or disengaged from the outer receptacle for allowing the tourmaline tiles to be easily cleaned or is replaced or changed with the new ones quickly and readily.

In accordance with one aspect of the invention, there is provided a steam physiotherapy mechanism comprising a receptacle including a housing, and a chamber formed in the housing, a platform disposed in the housing, a steam pipe disposed in the housing, a steam generating device connected to the steam pipe for generating and supplying a steam into the chamber of the housing, a number of tiles disposed in the chamber of the housing, and a number of retainers disposed in the chamber of the housing and engaged with the tiles for anchoring the tiles in the chamber of the housing, wherein the tiles each include a number of casings, and a compartment formed in each of the casings, and a number of compartment of the casings are filled with an ore mud, and the tiles are arranged to be easily and quickly removed or detached or disengaged from the outer receptacle for allowing the tiles to be easily cleaned or replaced or changed with the new ones quickly and readily.

The tiles each include a number of passages formed in the casings for communicating the compartments of the casings with each other and for allowing the ore mud to be filled or engaged into the compartments of the casings through the passages of the casings respectively.

The receptacle includes a base member, and the housing is disposed on the base member. The receptacle includes a stand extended downwardly from the base member. The receptacle includes an exit provided in the base member. The housing includes a door.

The housing includes an inclined peripheral flange extended radially and inwardly from an upper portion of the housing for forming a narrowed upper steam opening in the housing. The steam pipe includes a number of orifices formed in an inner peripheral portion of the steam pipe for allowing the steam to flow out of the steam pipe. The steam pipe includes a number of apertures formed in an outer peripheral portion of the steam pipe for allowing the steam to flow out of the steam pipe.

A dry sterilization apparatus may further be provided and includes a cover engaged onto the housing. The dry sterilization apparatus includes a switch attached to the cover, and a timer and a power indicating light and an operation indicating light and an ultraviolet (UV) germicidal lamp and an outlet and a recycling arrangement attached to the cover.

Further objectives and advantages of the present invention will become apparent from a careful reading of the detailed description provided hereinbelow, with appropriate reference to the accompanying drawings.

BRIEF DESCRIPTION OF THE DRAWINGS

FIGS. 9 and 10 are partial perspective views illustrating a tourmaline tile of the steam physiotherapy mechanism;

FIGS. 11 and 12 are other partial perspective views illustrating the other arrangement of the tourmaline tile;

DETAILED DESCRIPTION OF THE PREFERRED EMBODIMENT

Figure 1:
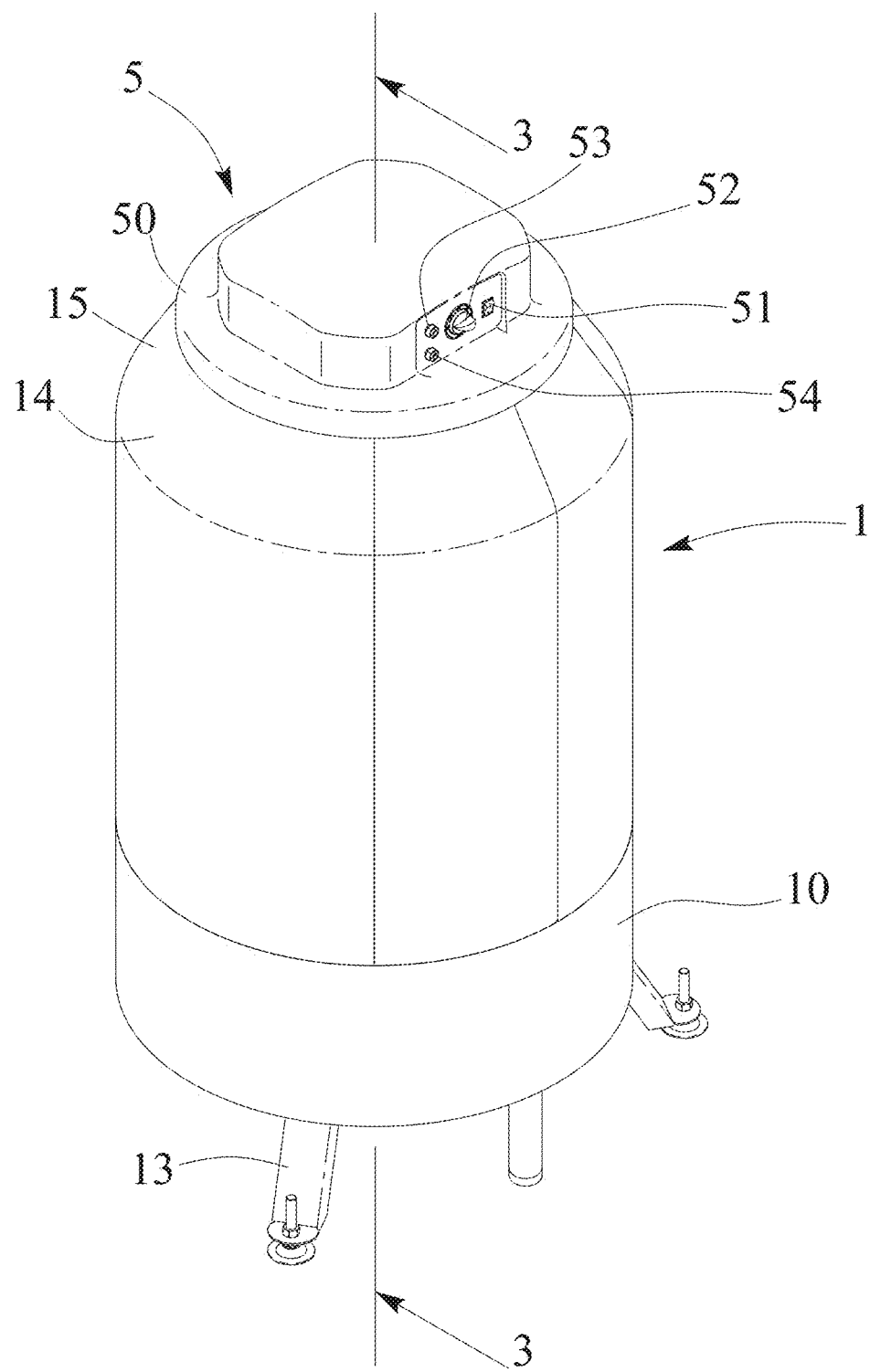
FIG. 1 is a perspective view of a steam physiotherapy mechanism in accordance with the present invention.
Figure 2:
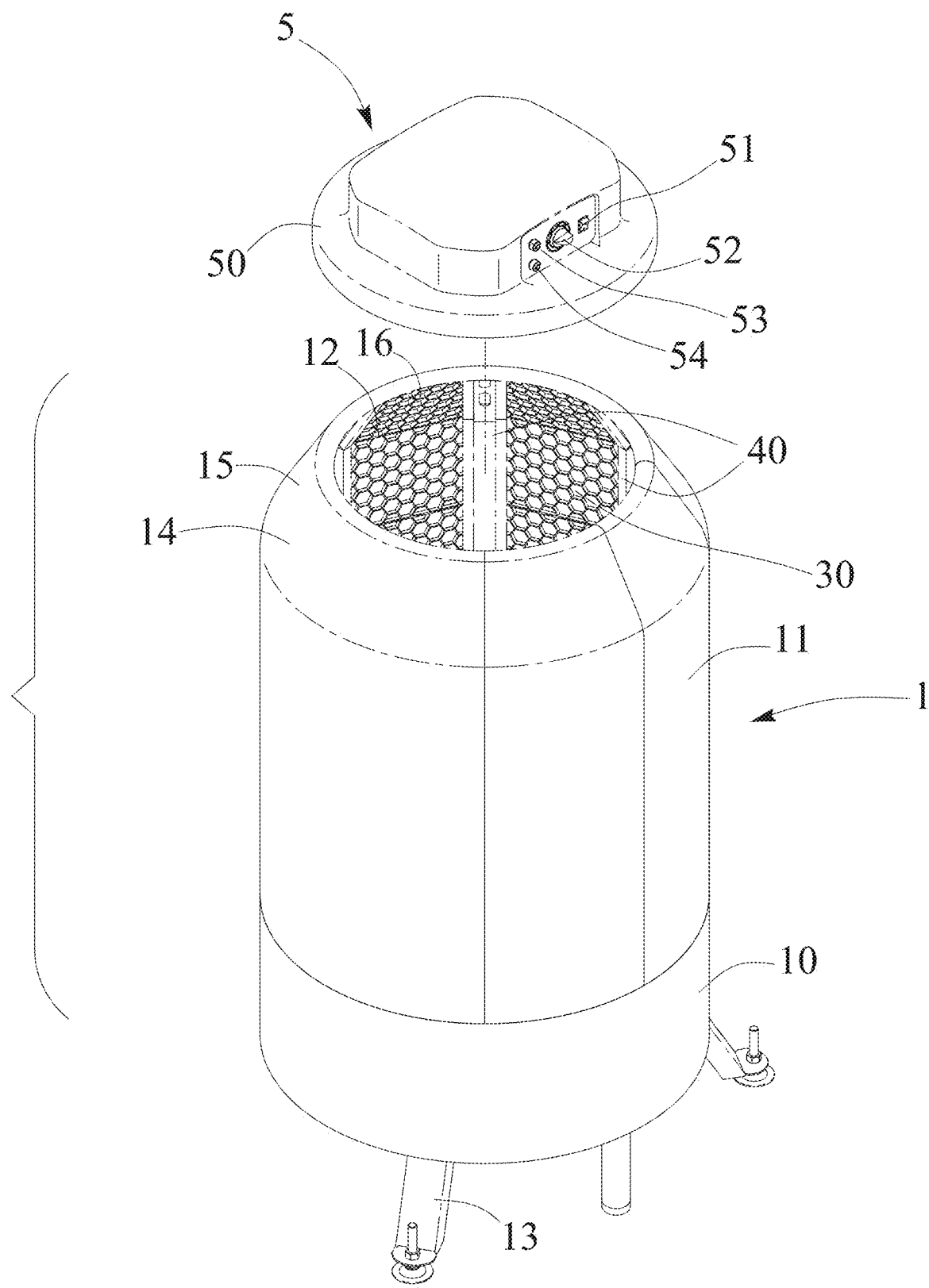
FIG. 2 is a partial exploded view of the steam physiotherapy mechanism.

Referring to the drawings, and initially to FIGS. 1-8, a steam physiotherapy mechanism in accordance with the present invention comprises an outer housing or outer receptacle 1 for receiving or accommodating the user therein, and the receptacle 1 includes a lower base member 10 and an upper container or housing 11 disposed or attached or mounted or secured on the base member 10 for forming or defining a chamber 12 within the housing 11 and/or the base member 10 and for receiving or accommodating the user within the chamber 12 within the housing 11 and/or the base member 10. A foot or stand 13 is disposed or provided in the lower or bottom portion of the base member 10 and/or of the receptacle 1 and extended downwardly for suitably supporting the receptacle 1 in place. The housing 11 includes a tilted or inclined peripheral skirt or flange 14 extended radially and inwardly from the upper portion 15 of the housing 11 for forming or defining a narrowed upper steam opening 16 in the housing 11 and arranged for allowing the head of the user to outstretch his head and for suitably retaining the steam within the chamber 12 of the housing 11.

It is preferable that the housing 11 includes an openable entrance or door 17 (FIG. 7) arranged for allowing the user to easily enter into and come out of the housing 11 and/or the base member 10. A seat or chair or platform 20 is disposed or engaged in the housing 11 and/or the base member 10 of the receptacle 1 for suitably supporting the user within the chamber 12 of the housing 11 and/or the base member 10. It is preferable that the platform 20 includes a knob or handgrip 21 formed or provided in the platform 20 (FIGS. 3, 7-8) for allowing the platform 20 to be easily carried with the user. A steam inlet pipe 23 is provided in the physiotherapy chamber 12 of the housing 11 on a bottom thereof, and preferably disposed or engaged below the platform 20, and a steam generating unit or device 24 is connected or coupled to the steam inlet pipe 23 for generating and supplying or conveying the generated steam into the physiotherapy chamber 12 of the housing 11. The steam pipe 23 includes one or more orifices 25 (FIG. 6) formed or provided in the inner peripheral portion thereof, and one or more apertures 26 is formed or provided in the outer peripheral portion thereof for supplying the steam inwardly and outwardly therefrom.

The receptacle 1 includes a number of tourmaline tiles 30 disposed or engaged into the chamber 12 of the housing 11 and/or of the base member 10 for releasing far infrared rays and negative ions into the chamber 12 of the housing 11 in order to help removal of toxins from the user's body via capillaries and sweat glands, and a number of plates or panels or retainers 40 are also disposed or engaged into the chamber 12 of the housing 11 and/or of the base member 10 and contacted or engaged with the tourmaline tiles 30 for anchoring or retaining or positioning the tourmaline tiles 30 within the chamber 12 of the housing 11 and/or of the base member 10. As shown in FIGS. 9-14, the tourmaline tiles 30 each include a number of honeycomb casings 31 formed or provided therein, and the casings 31 each include a chamber or compartment 32 formed therein, and a number of holes or passages 33 formed in the casings 31 for communicating the compartment 32 of the casings 31 with each other. In operation, an ore mud 34 (FIG. 14) will be filled into the compartment 32 of the casings 31 and will be solidly adhered or hardened or secured to the casings 31 with heating operations or the like.

Figure 3:
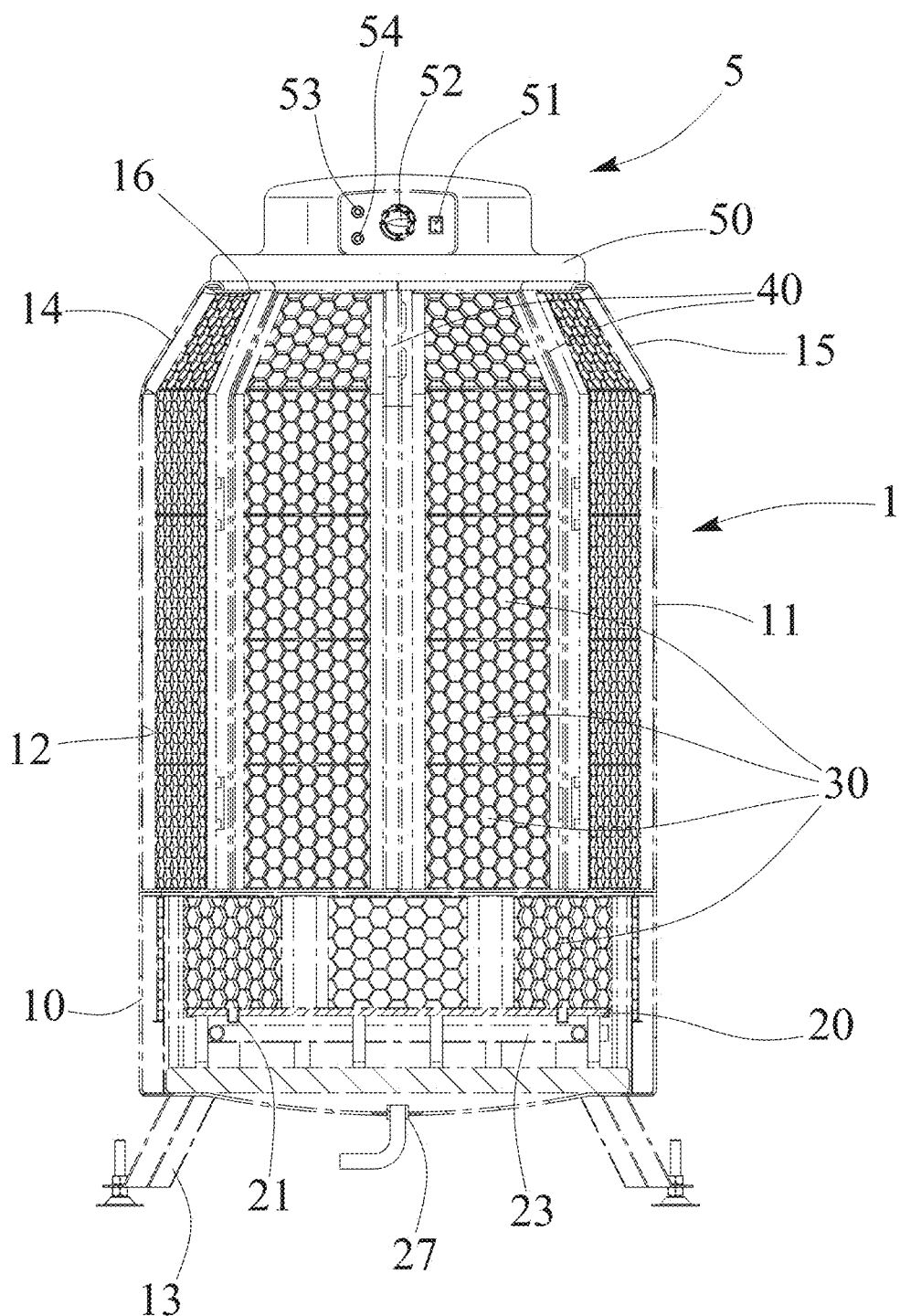
FIG. 3 is a cross sectional view of the steam physiotherapy mechanism, taken along lines 3-3 of FIG. 1.
Figure 8:
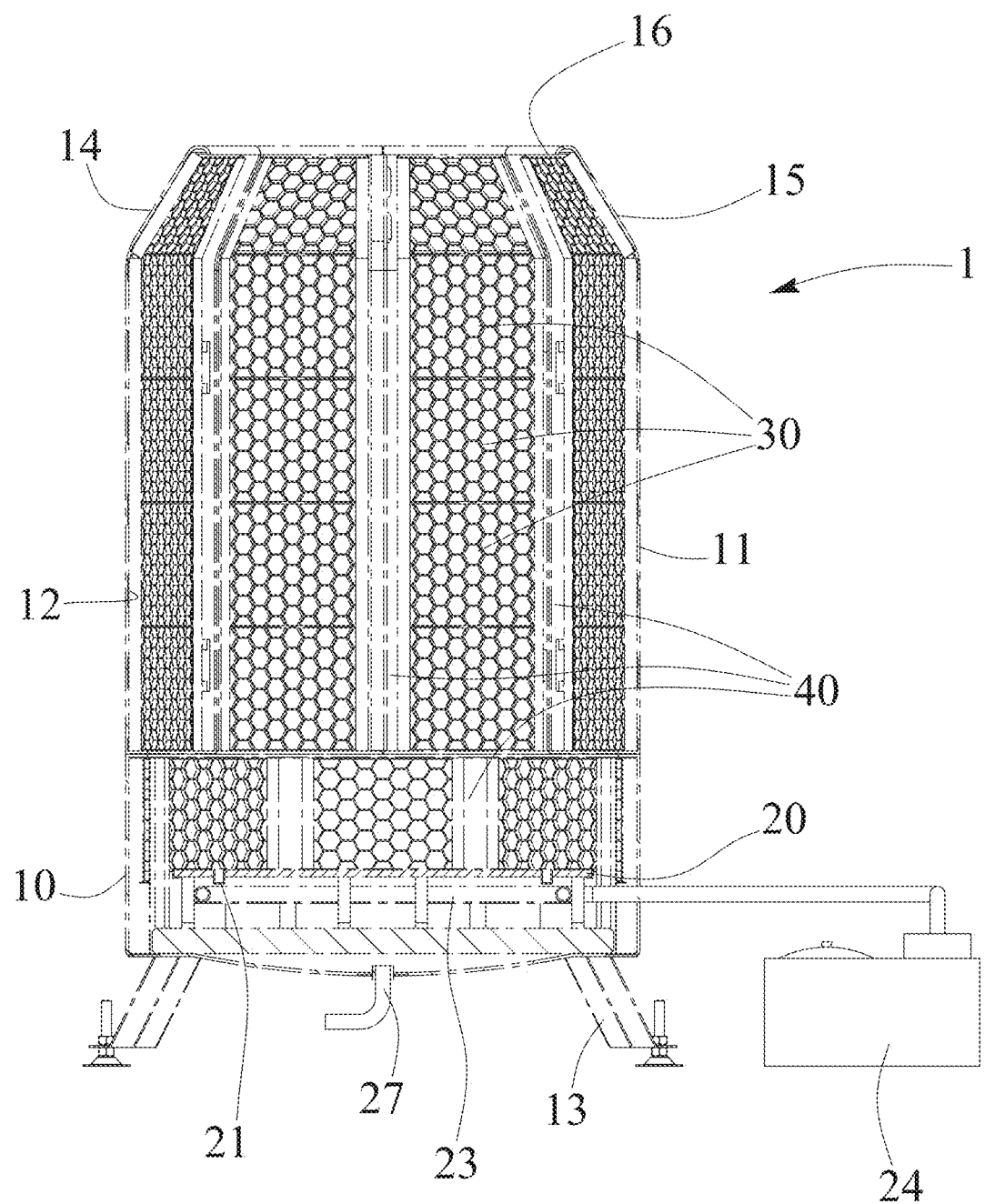
FIG. 8 is a cross sectional view of the steam physiotherapy mechanism, taken along lines 8-8 of FIG. 5.
Figure 12:
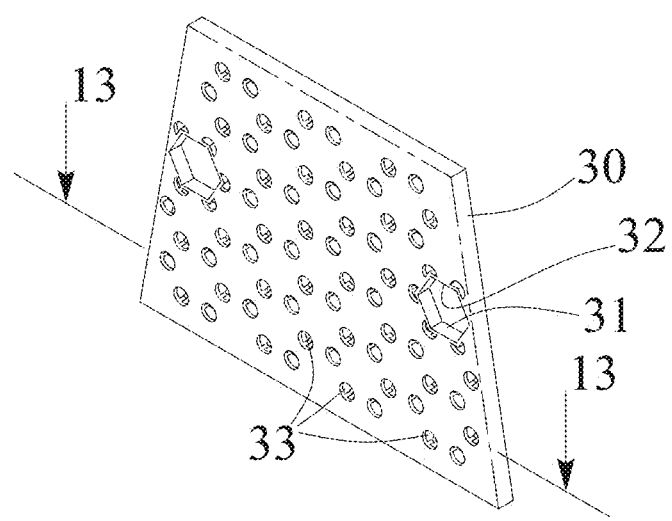
Figure 13:
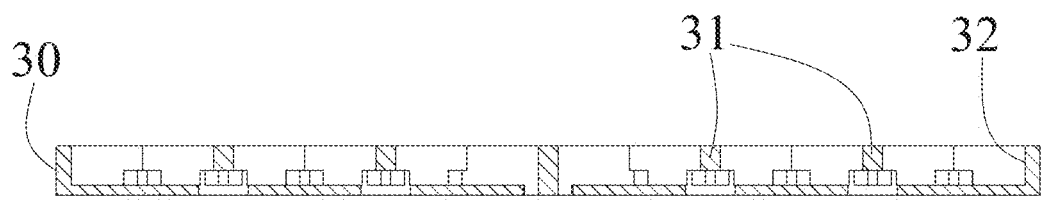
FIG. 13 is a cross sectional view of the steam physiotherapy mechanism, taken along lines 13-13 of FIG. 12.
Figure 14:
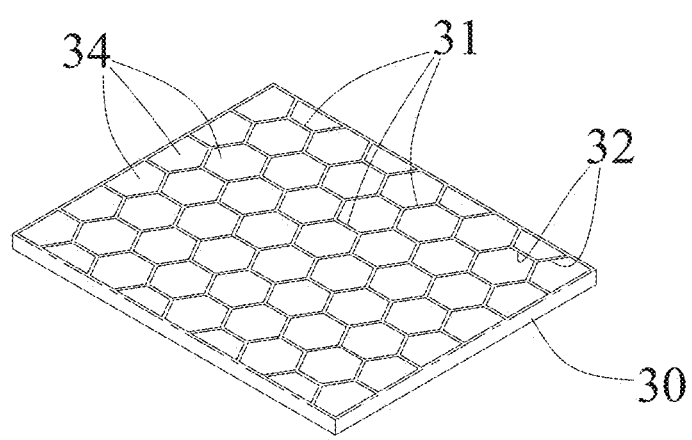
FIG. 14 is a perspective view illustrating the tourmaline tile of the steam physiotherapy mechanism.

It is to be noted that the ore mud 34 may be filled into the compartment 32 of the casings 31 and also be filled into the passages 33 of the casings 31 for allowing the ore mud 34 to be solidly adhered or hardened or secured to the casings 31 after the heating operations or the like. The tourmaline tiles 30 may then be attached or mounted or secured in the chamber 12 of the housing 11 and/or of the base member 10 with the retainers 40. As shown in FIGS. 10 and 12, one or more compartments 32 of the casings 31 may be selected without being filled or introduced with the ore mud and left empty. As shown in FIGS. 3 and 8, the receptacle 1 includes an outlet or exit 27 formed or provided in the lower or bottom portion of the base member 10 for allowing the water contained in the chamber 12 of the housing 11 and/or of the base member 10 to flow out of the base member 10 of the receptacle 1.

Figure 4:
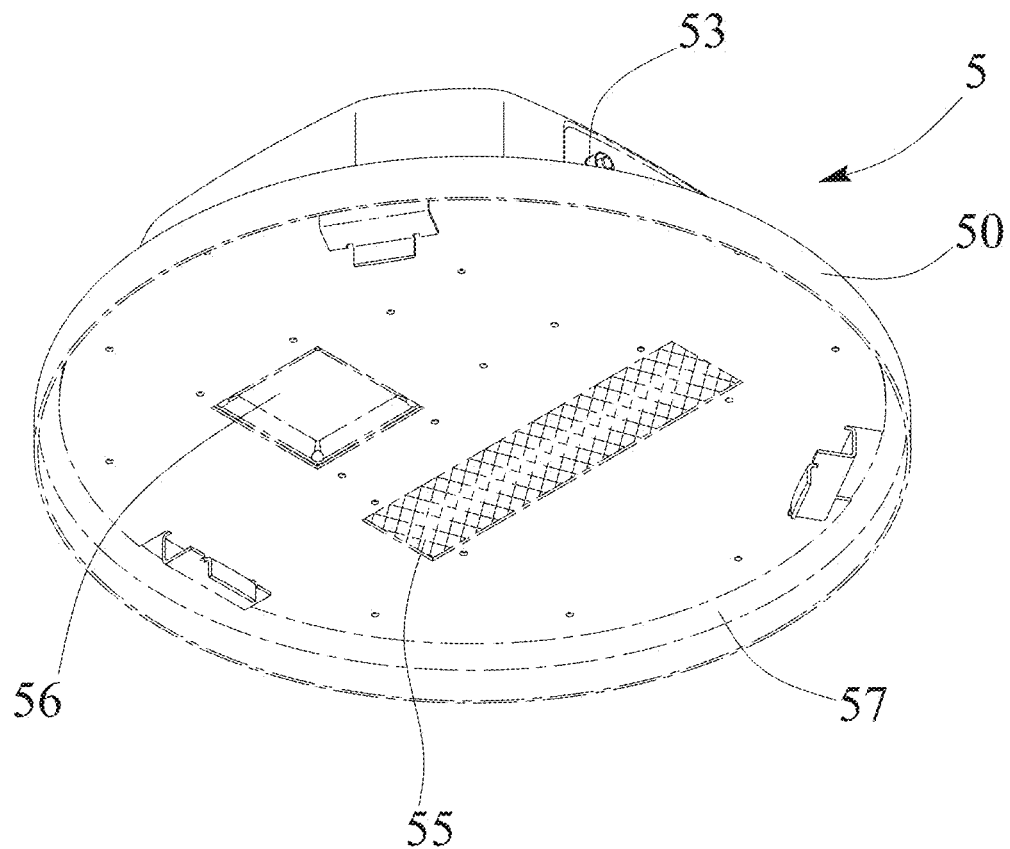
FIG. 4 is a partial perspective view illustrating a cover of the steam physiotherapy mechanism.

As shown in FIGS. 1-4, a dry sterilization unit or apparatus 5 includes a shield or cover 50 for attaching onto the tilted or inclined peripheral flange 14 at the upper portion 15 of the housing 11, a switch 51 attached or mounted or secured to the cover 50 for controlling or operating the dry sterilization apparatus 5, a timer 52 also attached or mounted or secured to the cover 50 for timing purposes, a power indicating light 53 also attached or mounted or secured to the cover 50 for indicating whether the power is on or not, an operation indicating light 54 also attached or mounted or secured to the cover 50 for indicating whether the dry sterilization apparatus 5 is suitably actuated or operated or not. As shown in FIG. 4, an ultraviolet (UV) germicidal lamp 55 is also attached or mounted or secured to the inner portion of the cover 50 for generating an ultraviolet (UV) and for sterilization purposes, the cover 50 includes an exit or outlet 56 formed or provided therein for allowing the hot air to flow out of the receptacle 1, and includes a recycling area or section or arrangement 57 for recycling the hot air and for economizing the energy.

Figure 5:
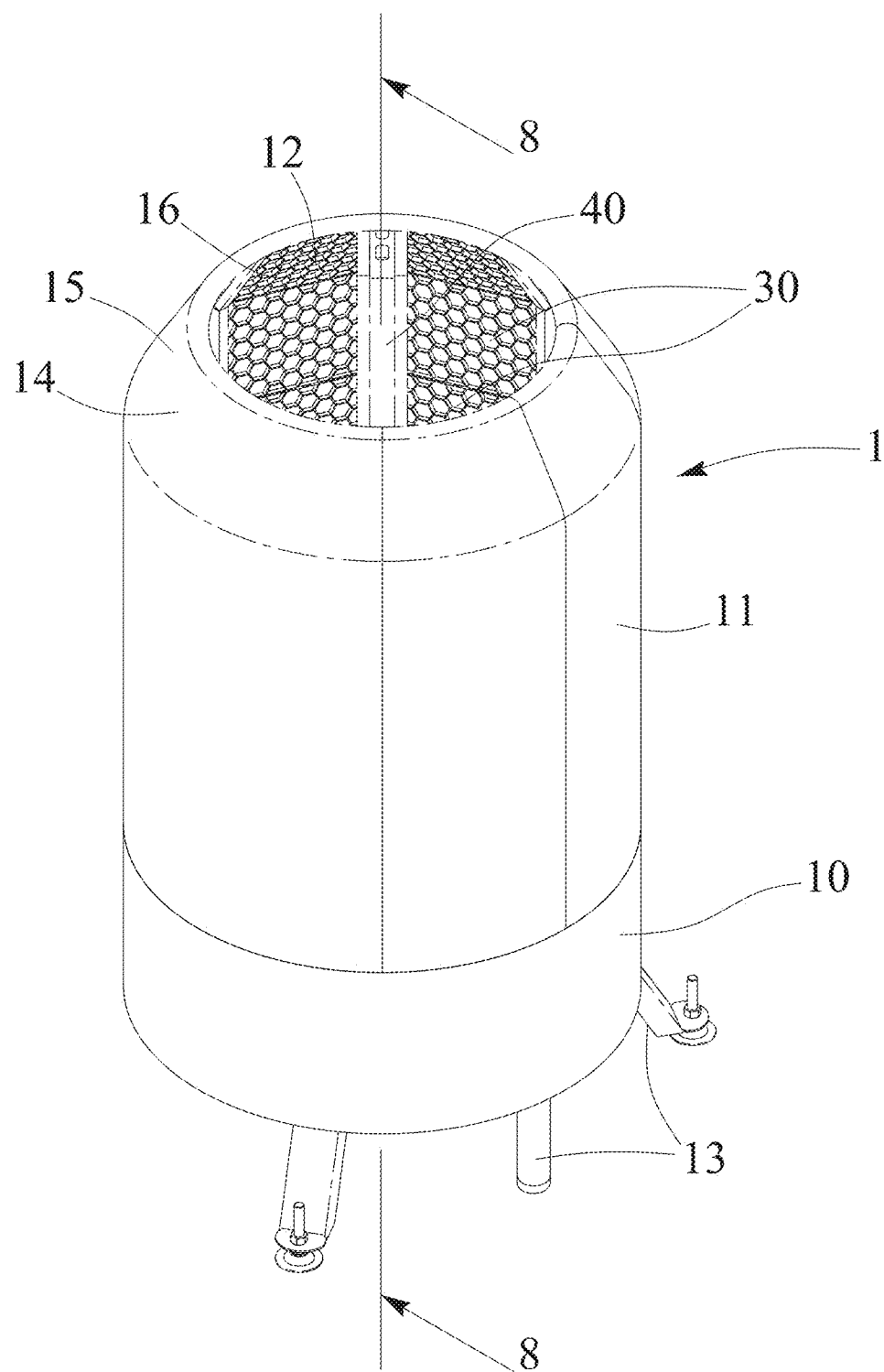
FIG. 5 is another perspective view of the steam physiotherapy mechanism with the cover removed.
Figure 6:
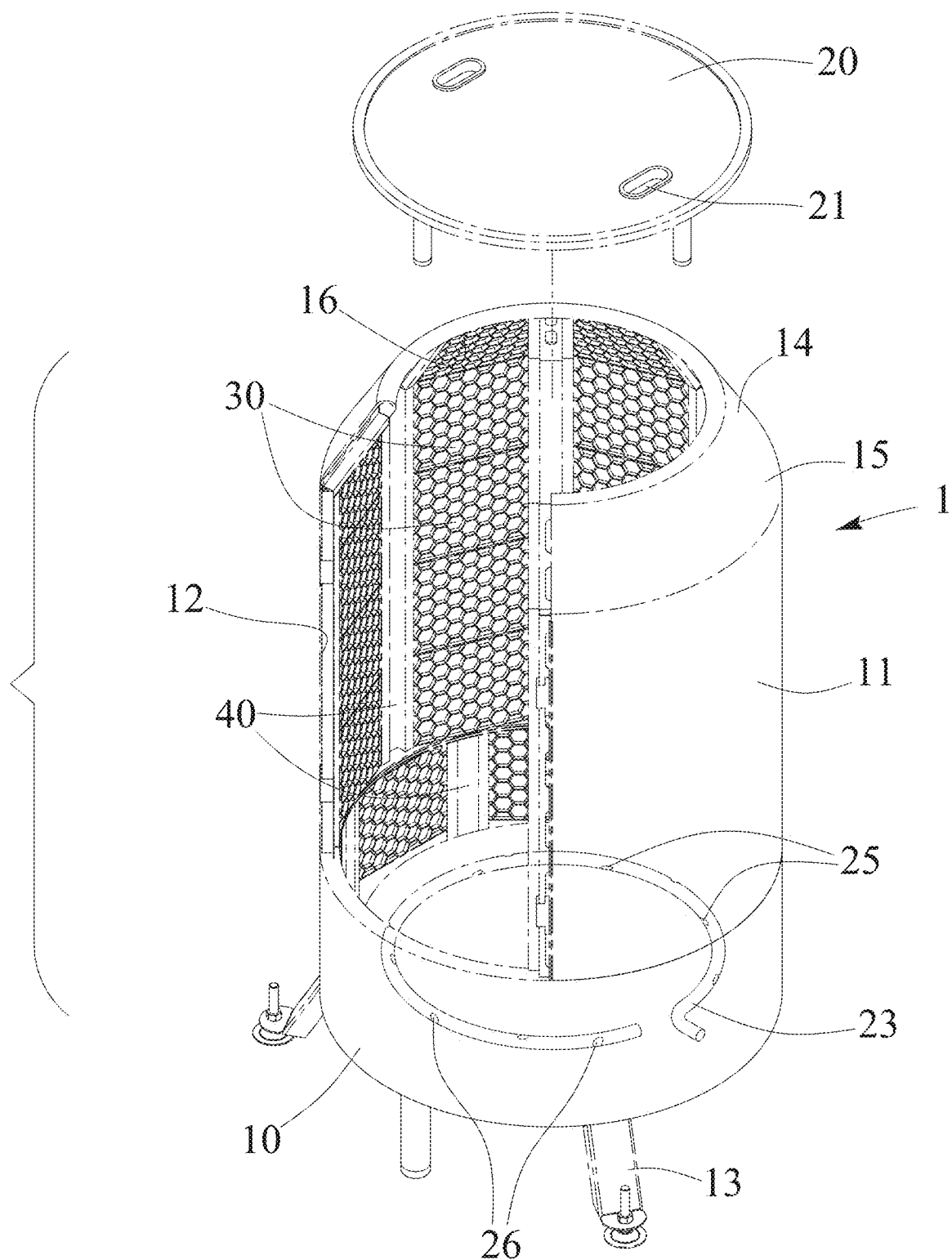
FIG. 6 is another partial exploded view of the steam physiotherapy mechanism as shown in FIG. 5.
Figure 7:
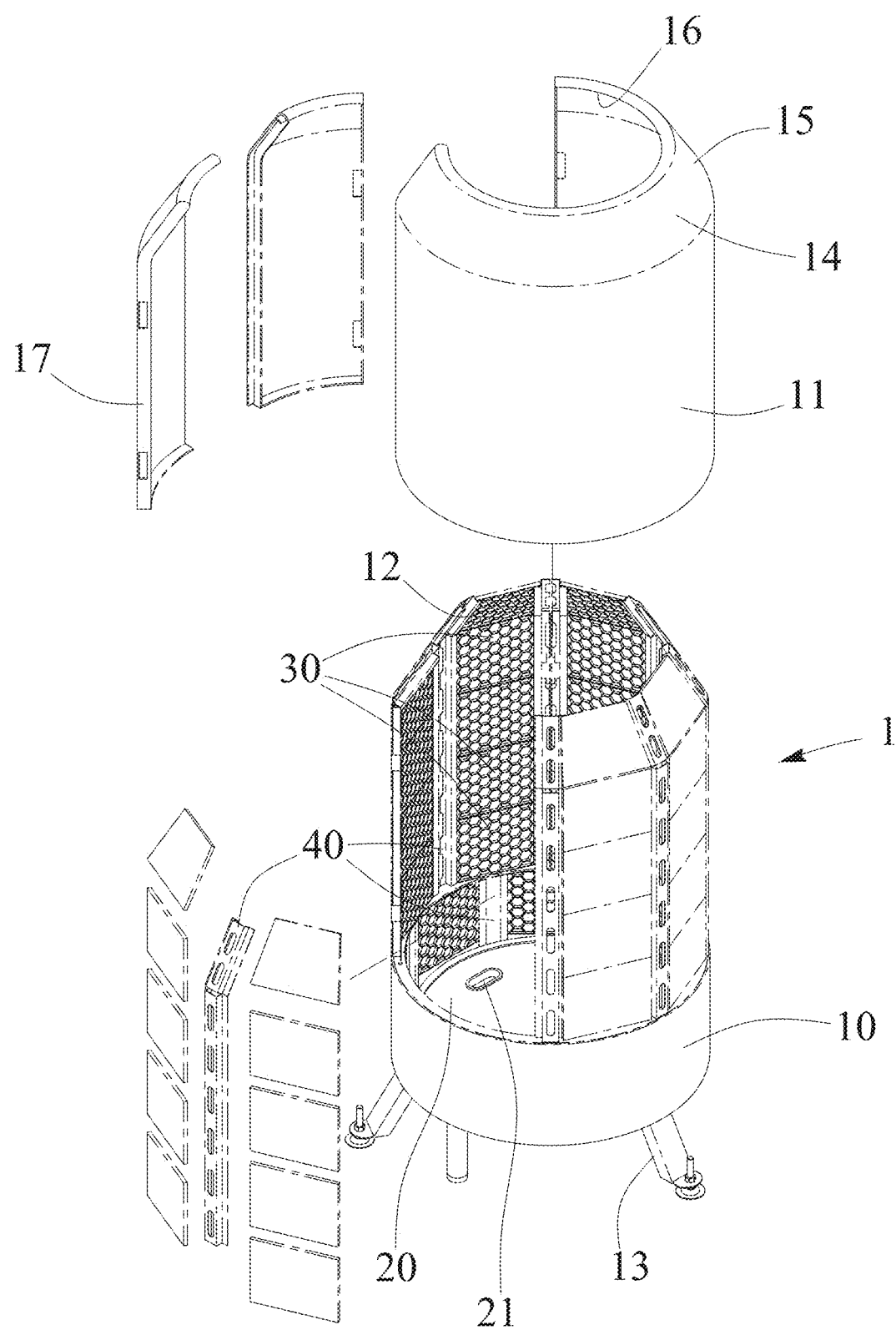
FIG. 7 is a further partial exploded view of the steam physiotherapy mechanism.

In operation, as shown in FIGS. 5 and 8, the user may enter into and/or sit on or be supported on the platform 20, and the steam generating device 24 may generate and supply or convey the steam into the chamber 12 of the housing 11 and/or of the base member 10 for forcing the sweat to flow out of the user's body, and the tourmaline tiles 30 may generate and supply or release far infrared rays and negative ions into the chamber 12 of the housing 11 and/or of the base member 10 in order to help removal of toxins from the user's body via capillaries and sweat glands, and the water contained in the chamber 12 of the housing 11 and/or of the base member 10 may flow out of the base member 10 of the receptacle 1 via or through the exit 27 of the base member 10 of the receptacle 1. After the operation, the tourmaline tiles 30 and/or the platform 20 and/or the steam pipe 23 may be removed or detached or disengaged from the receptacle 1 for allowing the tourmaline tiles and the base member 10 and the housing 11 of the receptacle 1 to be easily cleaned.

Accordingly, the steam physiotherapy mechanism in accordance with the present invention includes a number of tourmaline tiles that may be removed or detached or disengaged from the outer receptacle for allowing the tourmaline tiles to be easily cleaned or replaced or changed with the new ones quickly and readily.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:
1. A steam physiotherapy mechanism comprising:
a receptacle including a housing, and a chamber formed in said housing,
a platform disposed in said housing,
a steam pipe disposed in said housing, a steam generating device connected to said steam pipe for generating and supplying a steam into said chamber of said housing, a plurality of tiles disposed in said chamber of said housing, and a plurality of retainers disposed in said chamber of said housing and engaged with said tiles for anchoring said tiles in said chamber of said housing, wherein said tiles each include a plurality of casings, and a compartment formed in each of said casings, and at least one of said compartments of said casings is filled with an ore mud.

2. The steam physiotherapy mechanism as claimed in claim 1, wherein said tiles each include a plurality of passages formed in said casings for communicating said compartments of said casings with each other.

3. The steam physiotherapy mechanism as claimed in claim 1, wherein said receptacle includes a base member, and said housing is disposed on said base member.

4. The steam physiotherapy mechanism as claimed in claim 3, wherein said receptacle includes a stand extended downwardly from said base member.

5. The steam physiotherapy mechanism as claimed in claim 3, wherein said receptacle includes an exit provided in said base member.

6. The steam physiotherapy mechanism as claimed in claim 1, wherein said housing includes an inclined peripheral flange extended radially and inwardly from an upper portion of said housing for forming a narrowed upper steam opening in said housing.

7. The steam physiotherapy mechanism as claimed in claim 1, wherein said steam pipe includes a plurality of orifices formed in an inner peripheral portion of said steam pipe.

8. The steam physiotherapy mechanism as claimed in claim 1, wherein said steam pipe includes a plurality of apertures formed in an outer peripheral portion of said steam pipe.

9. The steam physiotherapy mechanism as claimed in claim 1, wherein said housing includes a door.

10. The steam physiotherapy mechanism as claimed in claim 1 further comprising a dry sterilization apparatus including a cover engaged onto said housing.

11. The steam physiotherapy mechanism as claimed in claim 10, wherein said dry sterilization apparatus includes a switch attached to said cover.

12. The steam physiotherapy mechanism as claimed in claim 10, wherein said dry sterilization apparatus includes a timer attached to said cover.

13. The steam physiotherapy mechanism as claimed in claim 10, wherein said dry sterilization apparatus includes a power indicating light attached to said cover.

14. The steam physiotherapy mechanism as claimed in claim 10, wherein said dry sterilization apparatus includes an operation indicating light attached to said cover.

15. The steam physiotherapy mechanism as claimed in claim 10, wherein said dry sterilization apparatus includes an ultraviolet (UV) germicidal lamp attached to said cover.

16. The steam physiotherapy mechanism as claimed in claim 10, wherein said dry sterilization apparatus includes an outlet attached to said cover.

17. The steam physiotherapy mechanism as claimed in claim 10, wherein said dry sterilization apparatus includes a recycling arrangement attached to said cover.

* * * * *